United States Patent
Adinata

(10) Patent No.: US 8,240,069 B2
(45) Date of Patent: Aug. 14, 2012

(54) SNOW SHOVEL WITH SPRING LOADED SHOVEL HEAD

(76) Inventor: Yohans S. Adinata, Toronto (CA)

( * ) Notice: Subject to any disclaimer, the term of this patent is extended or adjusted under 35 U.S.C. 154(b) by 326 days.

(21) Appl. No.: 12/585,173

(22) Filed: Sep. 8, 2009

(65) Prior Publication Data

US 2009/0320331 A1     Dec. 31, 2009

Related U.S. Application Data

(63) Continuation-in-part of application No. 11/732,619, filed on Apr. 4, 2007, now Pat. No. 7,741,469.

(51) Int. Cl.
*E01H 5/02* (2006.01)

(52) U.S. Cl. .......................................................... 37/285

(58) Field of Classification Search ............... 37/264, 37/265, 278, 284, 285; 294/54.5
See application file for complete search history.

(56) References Cited

U.S. PATENT DOCUMENTS

| | | | |
|---|---|---|---|
| 2,811,792 A * | 11/1957 | Cork, Jr. ......................... | 37/284 |
| 3,107,446 A | 10/1963 | Messinger | |
| 4,214,385 A | 7/1980 | Baranowski | |
| 4,302,894 A * | 12/1981 | Emma ............................. | 37/434 |
| 4,910,893 A * | 3/1990 | Asay ................................ | 37/281 |
| 5,511,327 A * | 4/1996 | Jurkowski et al. .............. | 37/285 |
| 5,581,915 A * | 12/1996 | Lobato ............................ | 37/285 |
| 6,053,548 A * | 4/2000 | Bowles, Jr. .................... | 294/54.5 |
| 6,523,839 B2 * | 2/2003 | Simmons et al. .......... | 280/47.34 |
| 7,305,779 B1 | 12/2007 | Purvis | |
| 2001/0045029 A1 * | 11/2001 | Fulton ............................. | 37/266 |
| 2006/0249964 A1 * | 11/2006 | Brazeau ....................... | 294/54.5 |

* cited by examiner

*Primary Examiner* — Thomas B Will
*Assistant Examiner* — Mai Nguyen

(57) ABSTRACT

The manually powered wheeled-levered shovel/launcher device for the purpose of snow removal, which has a handle, and shovel shaft pivoted to the handle at one end and a snow shovel head at the other end of the shovel shaft. A collapsible foldable wheel assembly acts as a fulcrum is attached to the device for easy handling a snow load. The shovel head is able to tilt downward against a spring-loaded mechanism for the purpose of altering the launch direction from upward direction due to centrifugal force around the wheel resting on the ground to forward direction when a sudden force downward is applied on the handle.

9 Claims, 16 Drawing Sheets

SNOW SHOVEL WITH SPRING LOADED SHOVEL HEAD

This application is a Continuation in Part of application Ser. No. 11/732,619, filed Apr. 4, 2007 now U.S. Pat. No. 7,741,469, (priority of Apr. 3, 2006 Provisional App Ser. No. 60/788,079) title SNOW SHOVEL, Inventor, Y S Adinata.

FIELD OF THE INVENTION

The present invention relates to snow shovel with a tilting shovel head for engaging snow and for ejecting it from the shovel head. The snow shovel has an integrated spring-loaded mechanism on a wheeled/levered shovel.

BACKGROUND OF THE INVENTION

Wheeled and/or levered snow shovels have been proposed, capable of scraping and gathering, lifting, dumping and launching quantities of material such as snow with a reduced amount of physical exertion and strain on the operator, especially on the spine.

U.S. Patent Application No. 20050160633 Inventor Mark Noonan filed on Jul. 28, 2005 discloses a relatively large wheeled shovel having a handle formed at the end of an elongated yoke, the yoke in the middle is supporting through a wheel axle of a large wheel for the purpose of picking up of a load, transporting it to a location, and propelling the load over-board with quick arm/body motion on the part of a person operating on the handle. The substantially waist-high wheel is adapted to receive the body force of an operator as an effective leverage through the handle and causes a recoil action from the wheel to enhance the throwing power of the apparatus of the invention, comprising the shovel, the wheel and the yoke as the driving member.

U.S. Patent Application No. 20050160632 inventor Cyril Williams filed on Jul. 28, 2005 discloses a wheeled shovel with pivot mounted behind the scoop. Upon activation of a release lever, the scoop head is allowed to rotate downward, hence dumping its load. A wheel assembly mounted to an intermediate portion of the frame supports the scoop in an inclined position. Furthermore, the wheel assembly acts as a fulcrum whereby downward pressure on the handlebars of the shovel elevates the scoop for ease of transport.

U.S. Pat. No. 6,735,887 issued to Mohiuddin Muzzammel on May 18, 2004 discloses a wheeled shovel with a pair of large wheels placed well behind the snow scoop.

U.S. Pat. No. 5,918,921 issued to Vernon Samuelson on Jul. 6, 1999 discloses a levered shovel with wheel assembly connected to approximately the centre of the handle shaft of a shovel, which wheel acts as a fulcrum for the shovel.

U.S. Pat. No. 5,511,327 issued to Marlin/Kevin Jurkowski on Apr. 30, 1996 discloses a cart-like structural wheeled shovel having a wheel centrally located. The wheel acts as a fulcrum in order to elevate the scoop by pressing downward on the handlebar.

U.S. Pat. No. 4,302,894 issued to Sam Emma on Dec. 1, 1981 discloses a cart-like structural wheeled shovel with wheel centrally positioned and manually operated lever and when lever is activated, it causes the scoop to rotate downward thus dumping the load off the scoop.

The present tilting shovel head has been developed to address these problems, and preventing slippage on ice, and in which the launch-off is due to centrifugal force which pivots around a wheel resting on the ground toward the operator.

The tilting shovel head is coupled with a spring-loaded mechanism which alters the centrifugal circular-upward force; hence the launch is diverted to a forward launch direction.

Although, the above devices each may be useful for its intended purpose, it would be beneficial to the field to have an alternative combination of wheel/lever shovel which overcomes these limitations.

BRIEF SUMMARY OF THE INVENTION

A device for removing and disposing of snow comprising:
a main handle portion defining a hand grip end and a pivot end;
a pivot on said pivot end of said main handle portion;
a shovel shaft defining first and second shovel shaft ends;
a pivot bearing between said first shovel shaft end and said second shovel shaft end being pivotally mounted on said pivot of said main handle portion, said shovel shaft being swingable between first and second positions;
a shovel head fixed to said second end of said shovel shaft;
a bump stop extending from said pivot end of said main handle portion, and lying adjacent to but spaced from said shovel shaft and defining a limit for swinging of said shovel shaft, at said second position;
spring means connected between said main handle portion and said shovel shaft operable to urge said shovel shaft into said first position, and said spring means being yieldable upon loading of said shovel head with snow to permit swinging of said shovel shaft into said second position, against said bump stop, and said spring means urging said shovel shaft and said shovel head to return back to said first position when the snow load is launched; and,
a foldable wheel assembly connected adjacent to said pivot end of said main handle portion.

The shovel head tilts back once the snow is launched-off the shovel head, due to springs or due to an alternate bendable plastic/rubber like compound member which retracts or bounce-back to its original length or straight-shape in a sudden manner which create an abrupt stop, which prevents snow to stick to and/or build-up on the shovel head.

The wheel assembly can be folded after each use in order to save space for storing purposes.

The handle can be removed after each use in order to save space for storing purposes.

The handle height can be quickly adjusted by means of telescoping to ensure ergonomic comfort to the operator.

IN THE DRAWINGS

DESCRIPTION OF A SPECIFIC EMBODIMENT

Figure 1:
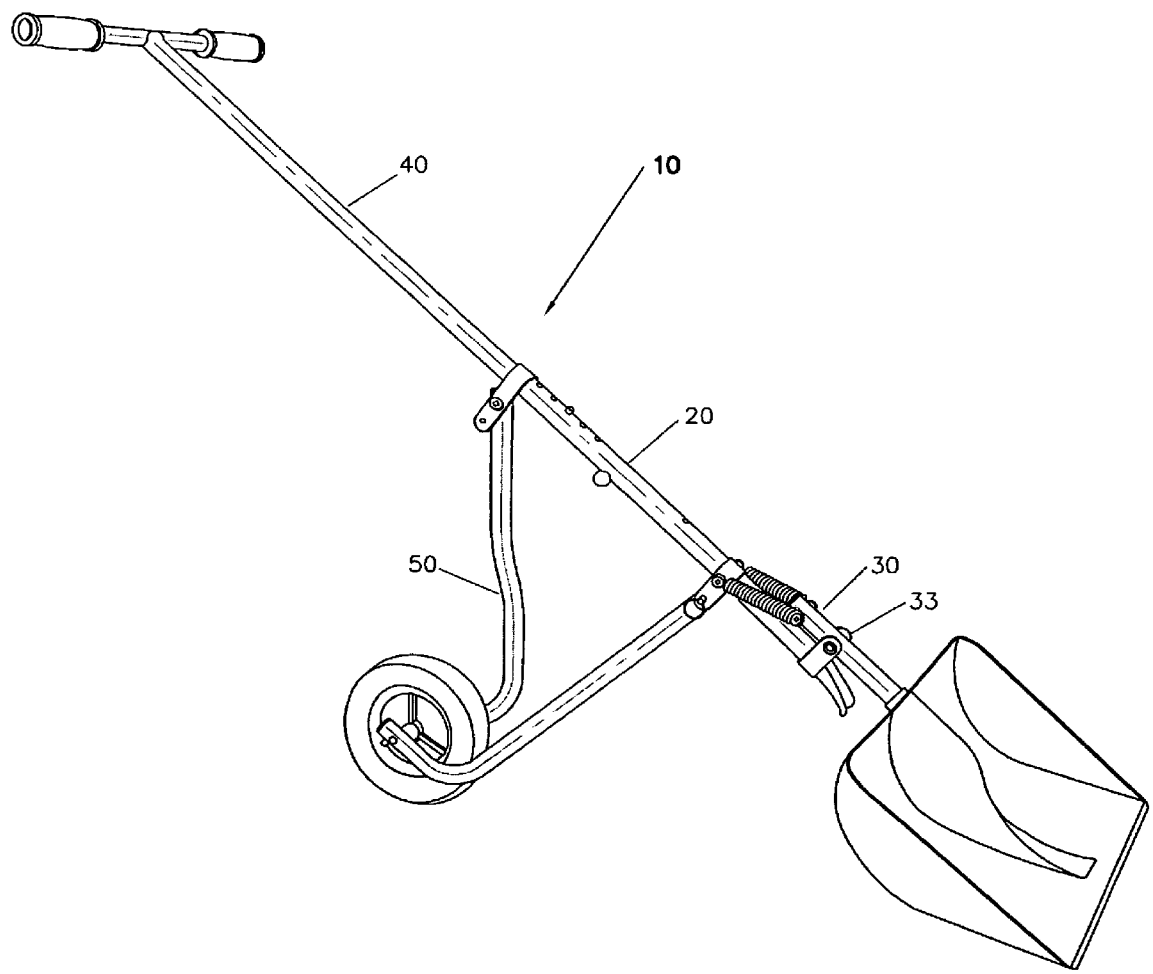
FIG. 1 is a three-dimensional view of the device showing wheel, T-shape handle at one end and shovel head assembly on the other end for gathering then launching snow load in particular.

Referring now to the drawings, FIG. 1 to 14, the details of preferred embodiments of the present invention are graphically and schematically illustrated.

As shown on FIG. 1, the wheeled-levered snow/launcher with tilting shovel head device 10 comprises a main handle portion 20, shovel assembly 30, telescopic shaft 40 and wheel assembly 50.

Figure 2:
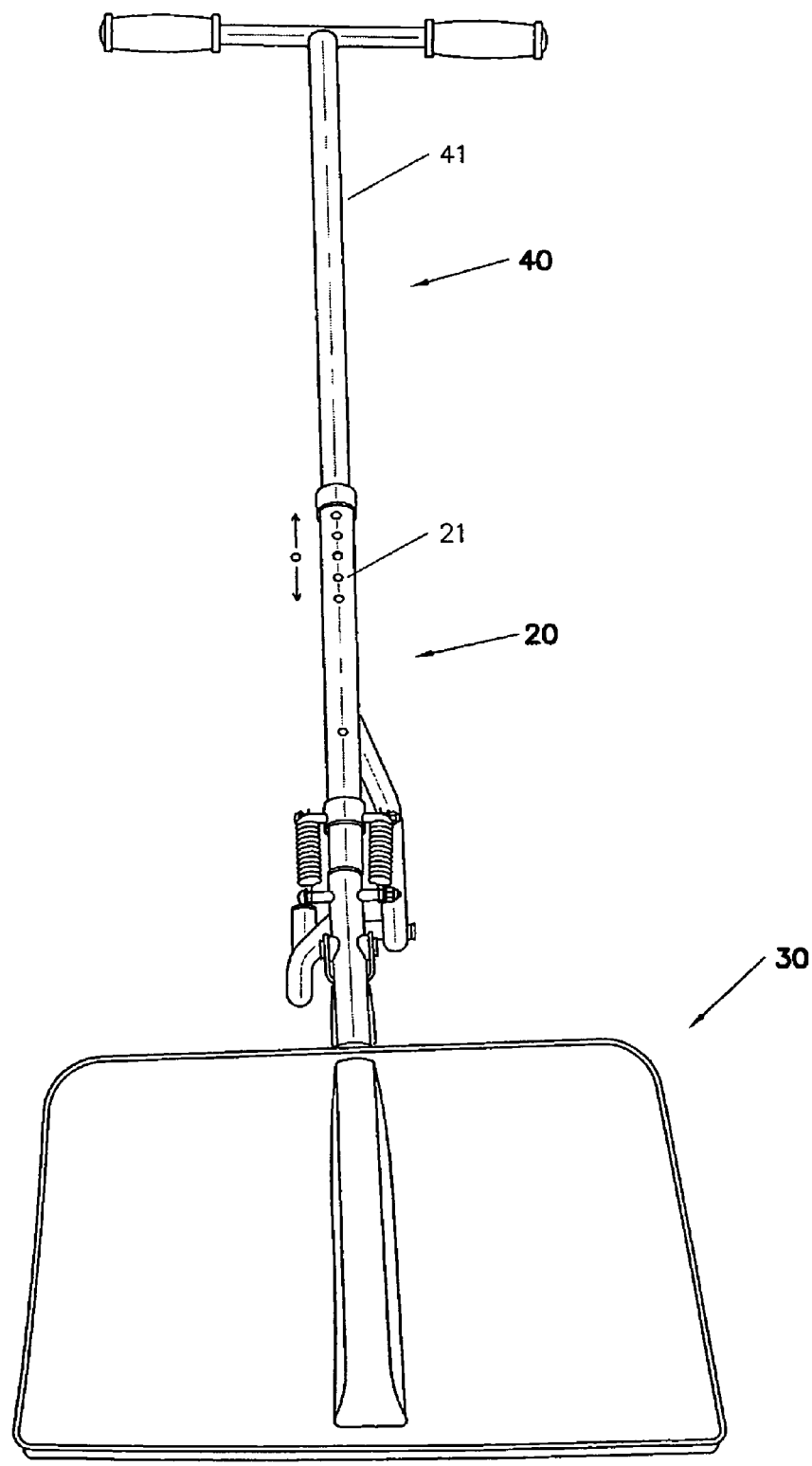
FIG. 2 is a front view of FIG. 1, showing the placement of shovel head assembly at the front and T-shape handle at the rear with one wheel.
Figure 2A:
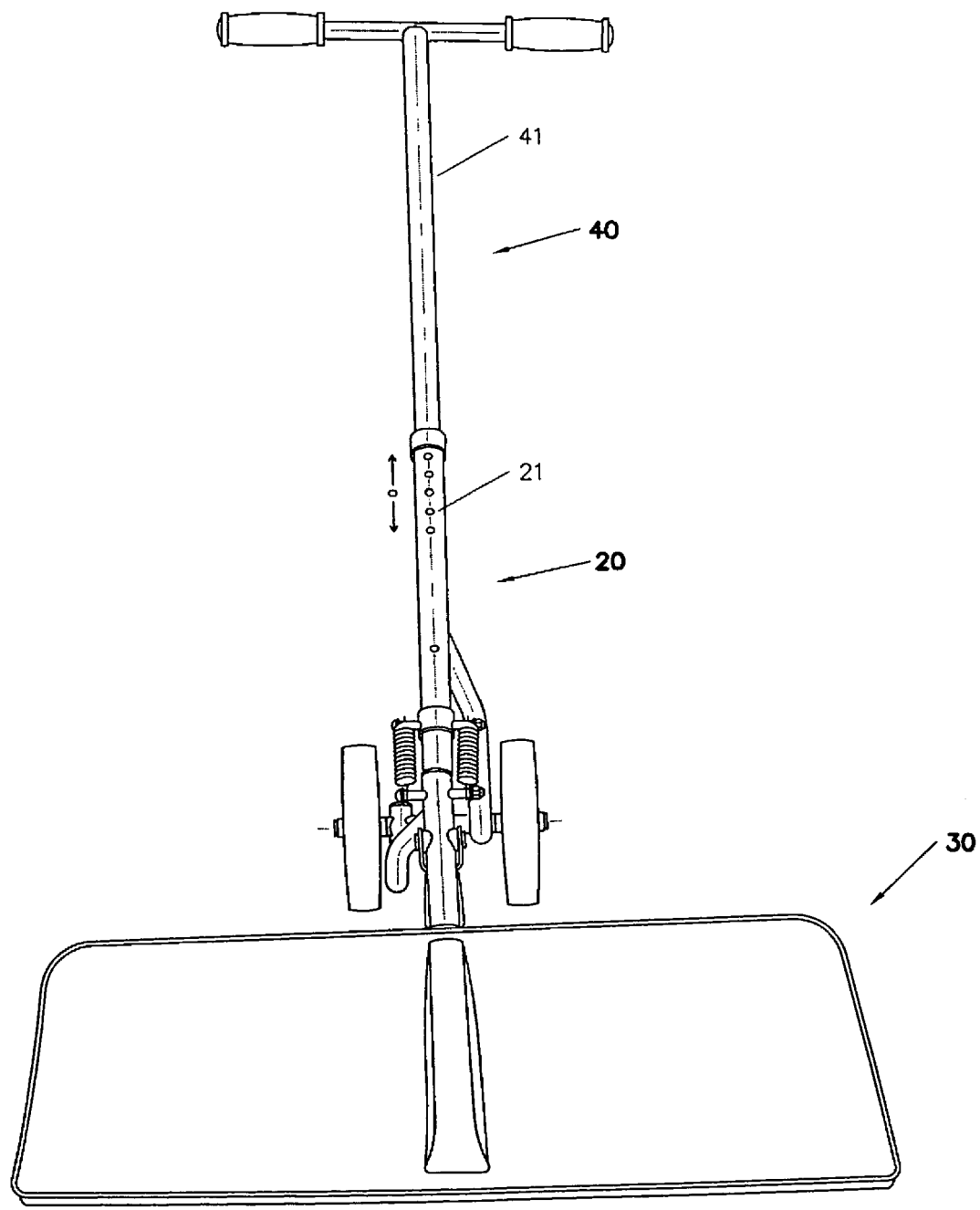
FIG. 2A is a front view of FIG. 1, showing the placement of shovel head assembly at the front and T-shape handle at the rear with two wheels to enhance stability on a larger/wider shovel head.

As shown on FIGS. 2 and 2A, telescopic shaft 40 is inserted in main handle 20 and can be adjusted up and down to suit operator height through different holes 21.

Clearly however the main handle portion and telescopic shaft could be made in one piece, where adjustment in length is not required.

In this case both the main handle portion and the telescopic shaft wold constitute the main handle.

Figure 3:
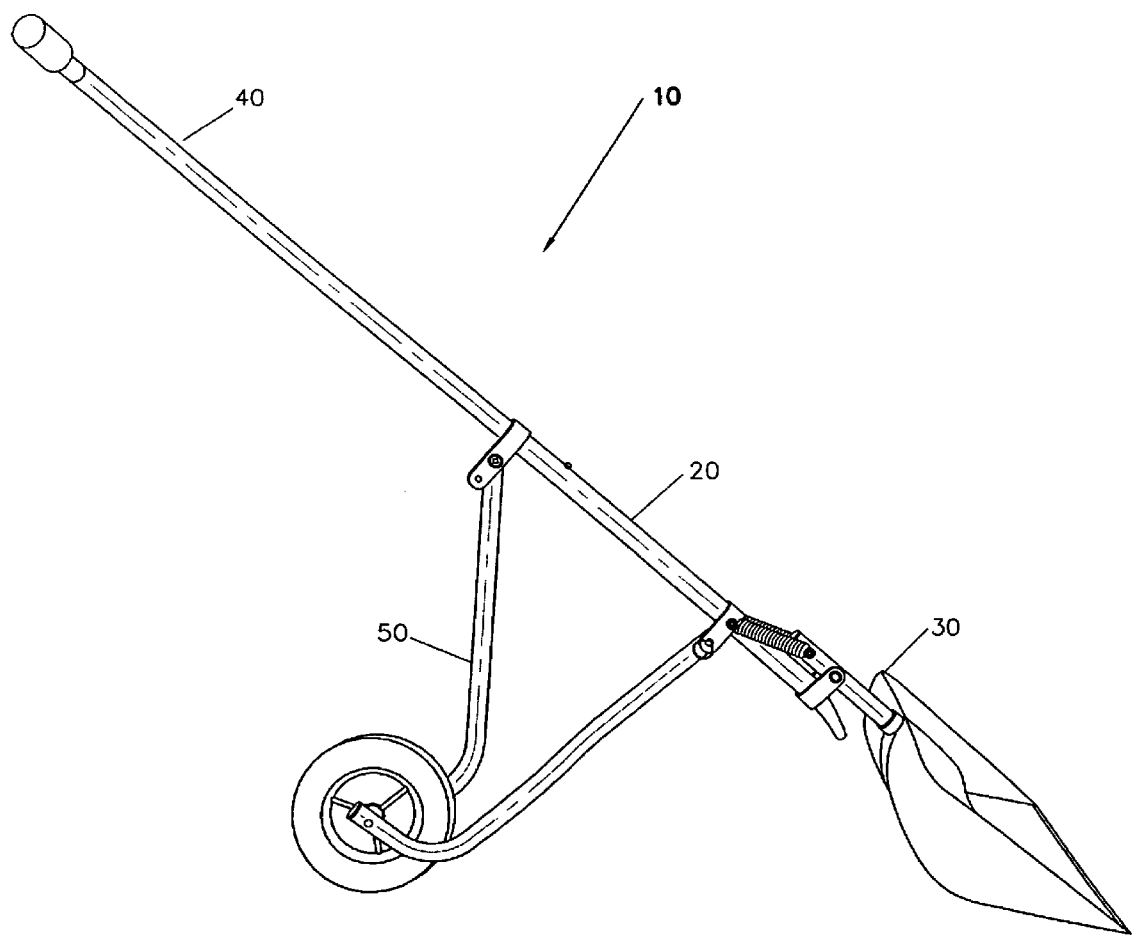
FIG. 3 is a side view of FIG. 2, showing the placement of shovel head assembly at one end and T-shape handle at the other end.

As shown on FIG. 3, is a side view of the device in gathering mode.

Figure 4:
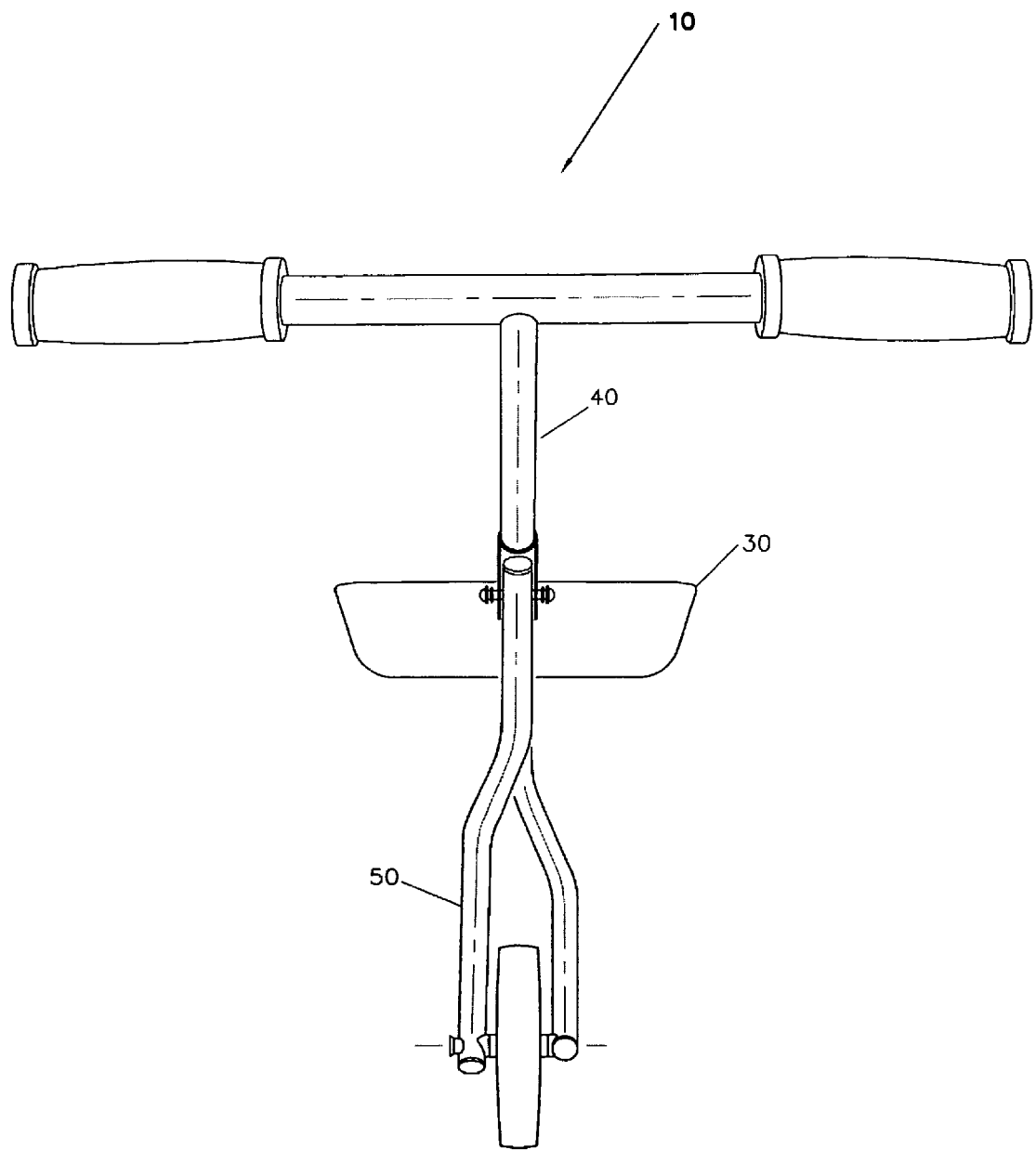
FIG. 4 is a rear view of FIG. 3, showing the device from the operator side with one wheel.

As shown on FIG. 4, is a rear view of the device with one wheel in gathering mode.

Figure 4A:
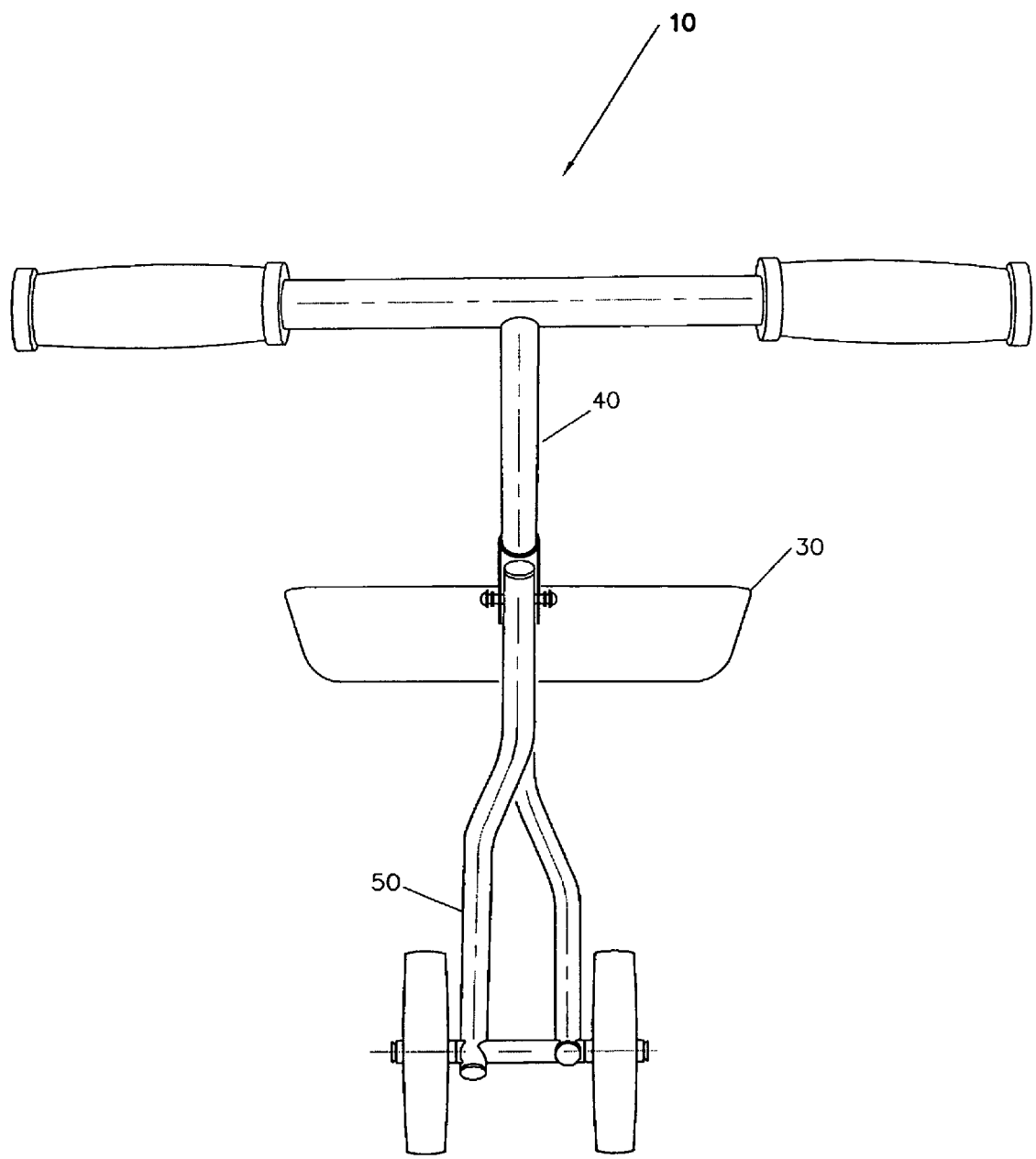
FIG. 4A is a rear view of FIG. 3, showing the device from the operator side with two wheels to enhance stability on a larger/wider shovel head.

As shown on FIG. 4A, is a rear view of the device with two wheels in gathering mode.

Figure 5:
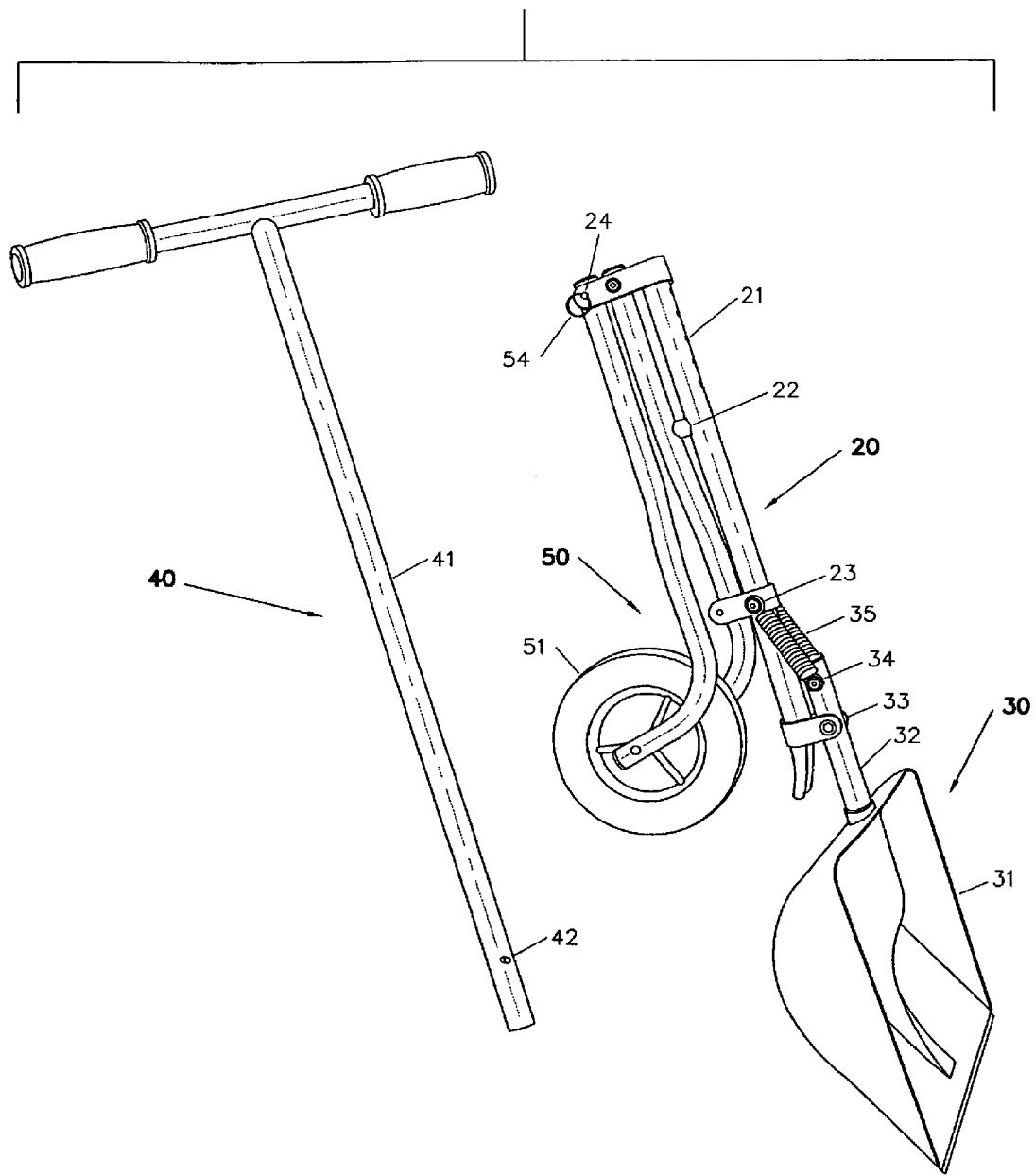
FIG. 5 is a three-dimensional view of the device with T-shape handle being detached and the wheel assembly being folded for space-saving storage.

As shown in FIG. 5; Shovel assembly 30 includes a shovel shaft 32 fixed to shovel head 31 at one end. At the other end of shovel shaft 32 a spring pin 34 secures one end of a spring arrangement 35. The other end of the spring arrangement is attached to the main handle at pivot 23

Midway between the first end and the second end of shovel shaft 32, shaft 32 is pivotally mounted in U-shaped pivot 33. Pivot 33 is mounted on the lower or pivot end of main handle 20.

Shovel shaft 32 can swing, in a see-saw fashion, in pivot 33, relative to handle 20. One end of springs 35 mount to spring mounting pin 34 on the first end of shovel shaft 32. Springs 35 are secured at their other ends to spring mounting pin 23, on main handle portion 20.

Wheel assembly 50 is separated from main handle portion 20 by spacer 22.

A spring-loaded snap-button 42 is used to secure telescopic shaft 40-41 to the desired one of holes 21 in main handle portion 20.

Locking-pin 54 is inserted in hole 24 in order to secure folded wheel assembly from opening up unintentionally while it is in folding mode for storage.

A bump stop 60 is secured to the lower end of main handle portion 20, so as to limit downward swinging of shaft 32. Bump stop 60 extends adjacent alongside part of shovel shaft 32. Bump stop 60 is positioned so as to engage shovel shaft 32, when the shovel is loaded with snow and swings down. In this way bump stop 60 acts as a limit to swinging movement of shovel shaft 32.

Wheel 51 is mounted on two separate arms namely a first arm 52 and a second arm 53. In the folded position both arms 52 and 53 are secured by a pin in first arm pivot 24.

Figure 6B:
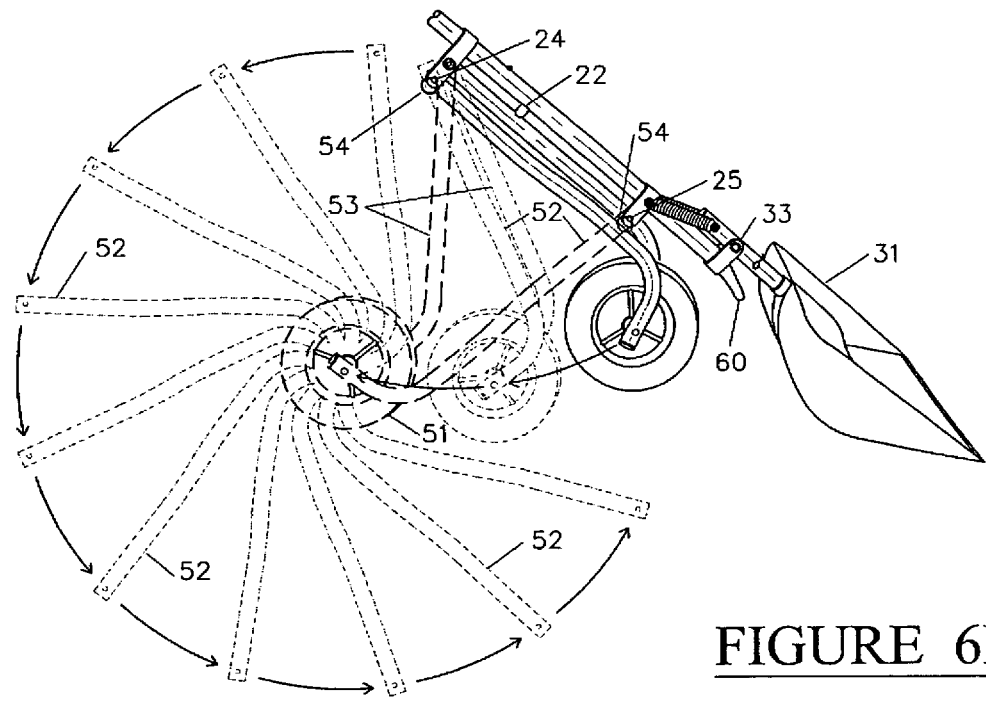
FIG. 6B is a wheel assembly unfolding sequence diagram by means of rotating method.
Figure 6A:
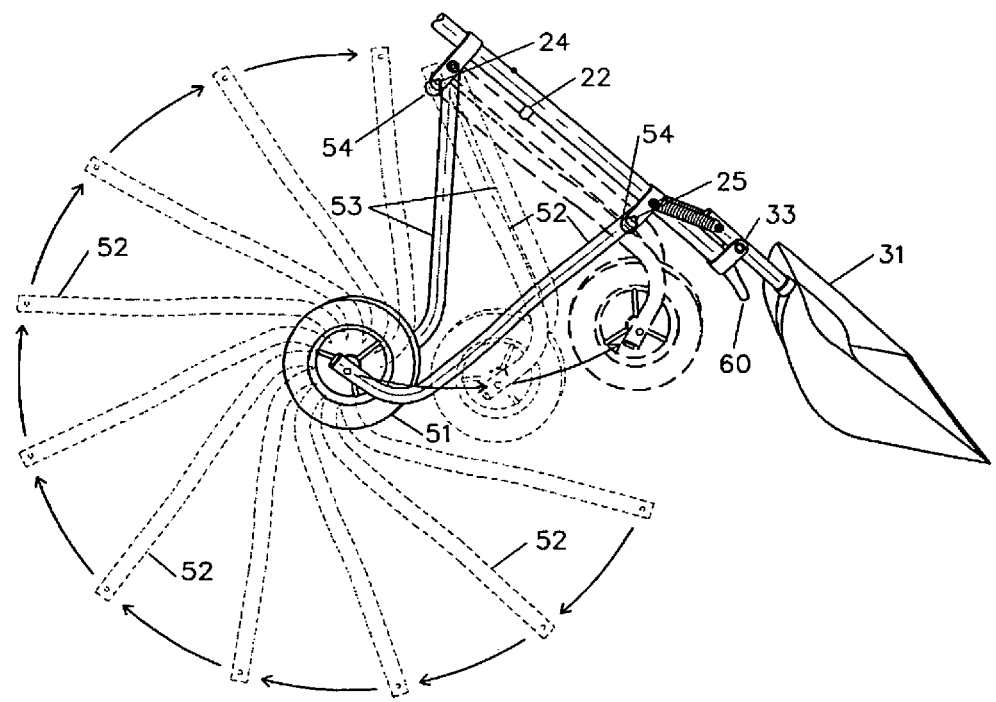
FIG. 6A is a wheel assembly folding sequence diagram by means of rotating method.

FIG. 6A shows the folding sequence with rotating method; By pulling-out locking-pin 54 from hole 25 in first arm pivot 24, arm 52 is free to rotate clockwise.

While rotating arm 52 clockwise, arm 53 will also rotate counter clockwise until the arm 53 reaches a stop at spacer 22, and where wheel 51 reaches a position behind shovel head 31. By continuing rotating of arm 52 it will line-up to first arm pivot 24, then locking pin 54 is inserted into hole 25 in order to secure folded wheel assembly from opening up unintentionally.

FIG. 6B shows the unfolding sequence with rotating method. By pulling-out locking-pin 54 from hole 24, arm 52 will free to rotate. By rotating arm 52 counter clockwise, arm 52 will eventually line-up to hole 25. Locking pin 54 is then inserted into hole 25 in order to secure wheel assembly in unfolded ready in-use position.

Figure 7B:
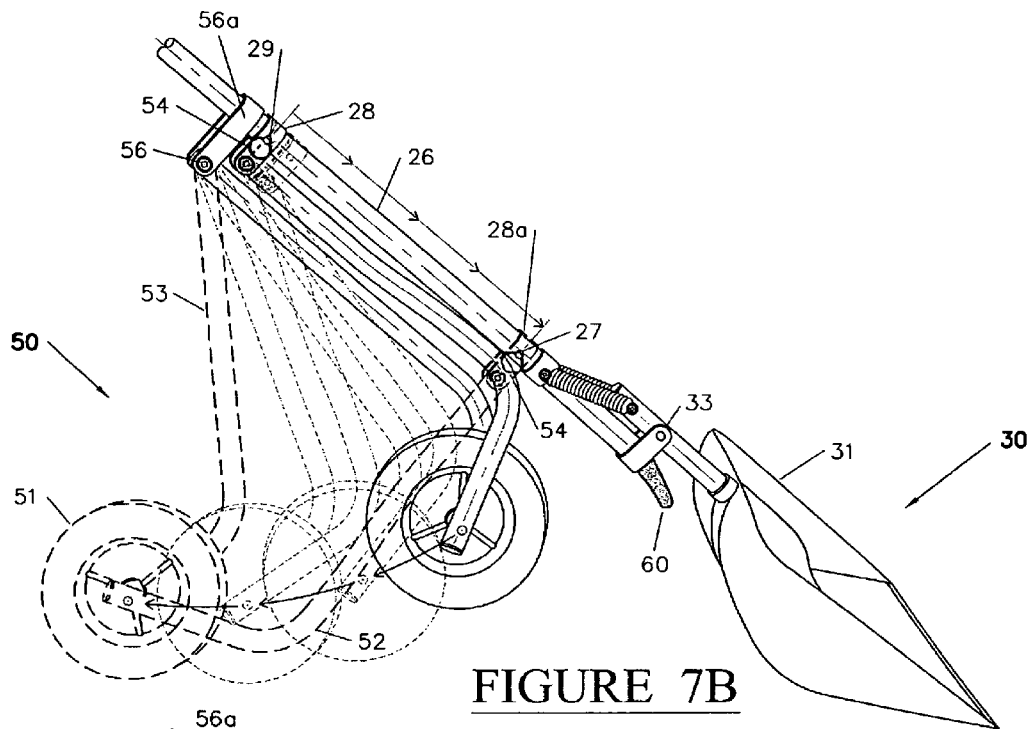
FIG. 7B is a wheel assembly unfolding sequence diagram by means of alternate sliding method.
Figure 7A:
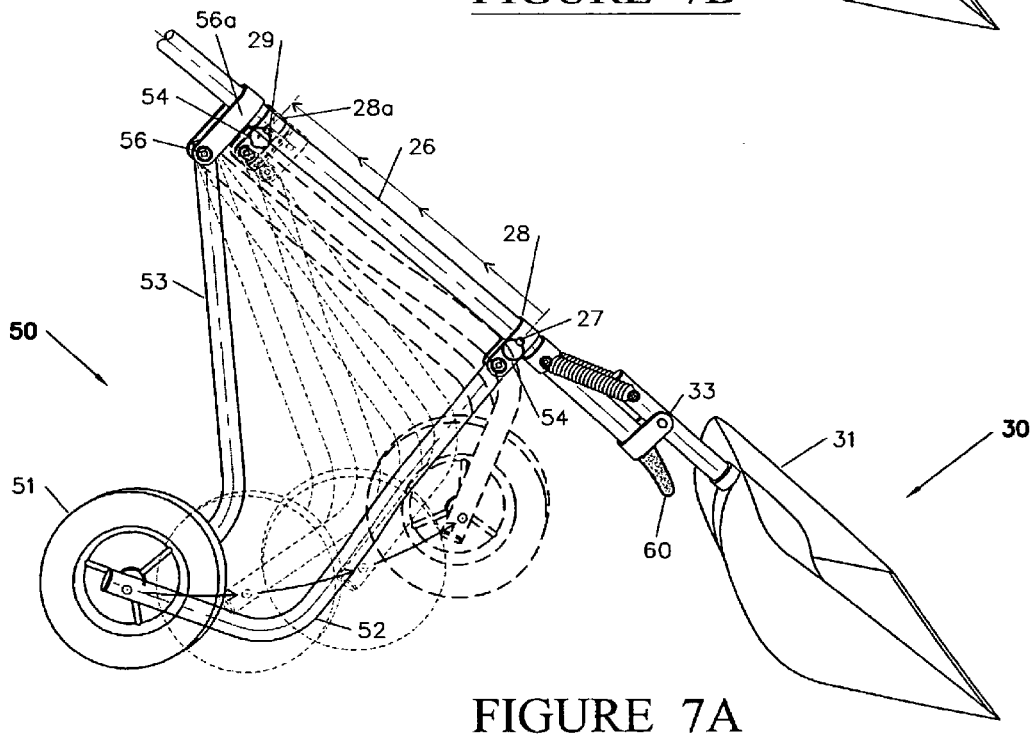
FIG. 7A is a wheel assembly folding sequence diagram by means of alternate sliding method.

FIG. 7A shows the folding sequence with sliding method;

In this embodiment a U-shaped bracket 56a is attached to handle 20. A pin 56 provides a first arm pivot for arm 53. A second arm pivot in the form of U shaped slide knuckle 28 is slidable along handle 20.

A locking pin 54 holds knuckle in the open position. By pulling-out locking-pin 54 from hole 27, arm 52 will free to rotate. By sliding knuckle 28 upward along handle 26, the wheel 51 also move forward, until knuckle 28 reaches its position at 28a, (FIG. 7a). Locking pin 54 is inserted through hole 29 in order to secure folded wheel assembly from opening up unintentionally.

FIG. 7B shows the unfolding sequence with sliding method; By pulling-out locking-pin 54 from hole 29, arm 52 will free to rotate, by sliding knuckle 28 downward along handle 26, the wheel 51 also move backward as a result until knuckle 28 reaches its position at 28a, then locking pin 54 is inserted through hole 27 in order to secure wheel assembly in unfolded ready in-use position.

Figure 8D:
FIG. 8D is an operation diagram, indicating handle/shovel head relations to the operator at Launched-Off.
Figure 8A:
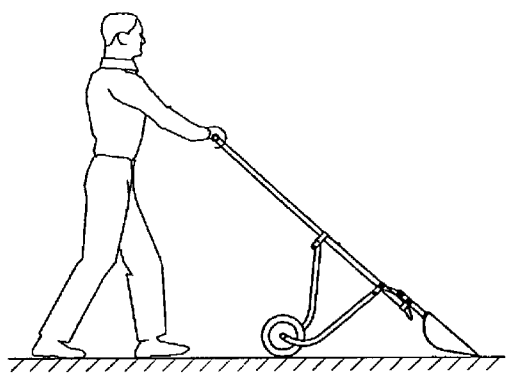
FIG. 8A is an operation diagram, indicating handle/shovel head relations to the operator at Gathering, Load stage.

FIG. 8A shows the gathering load function. In this operation the operator pushes the device forward, causing the snow to accumulate in the shovel head.

Figure 8C:
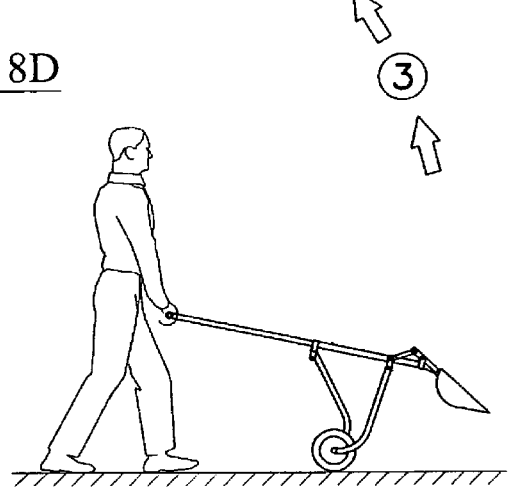
FIG. 8C is an operation diagram, indicating handle/shovel head relations to the operator at Final Launch.
Figure 8B:
FIG. 8B is an operation diagram, indicating handle/shovel head relations to the operator at Initial Launch.

FIG. 8B shows the initial launch function. When the operator introduces a sudden force (jerk) downward on the handle this causes the shovel head on the other end to receive an additional artificial load which overcomes the designed spring-rate of the springs 35. This causes the springs to extend and the shovel head assembly tilts downward. Downward swinging is checked by bump stop 60.

FIG. 8C shows the final launch function. The operator pushes down on the handle quickly. The entire device then rotates toward the operator around the wheel resting on the ground. Centrifugal force is created in which the force being used to launch the load, not in upward direction but rather in diagonal forward direction due to tilted downward position of the shovel head, and shaft 32 which is resting against the bump stop 60.

FIG. 8D shows the launched-off being completed. The springs 35 will retract to the original length in a sudden manner. The shaft 32 then swings up until is abuts on handle 20. At this point it abruptly bottoms-out. This creates an abrupt stop, which prevent any snow to stick to the shovel head.

Figure 9:
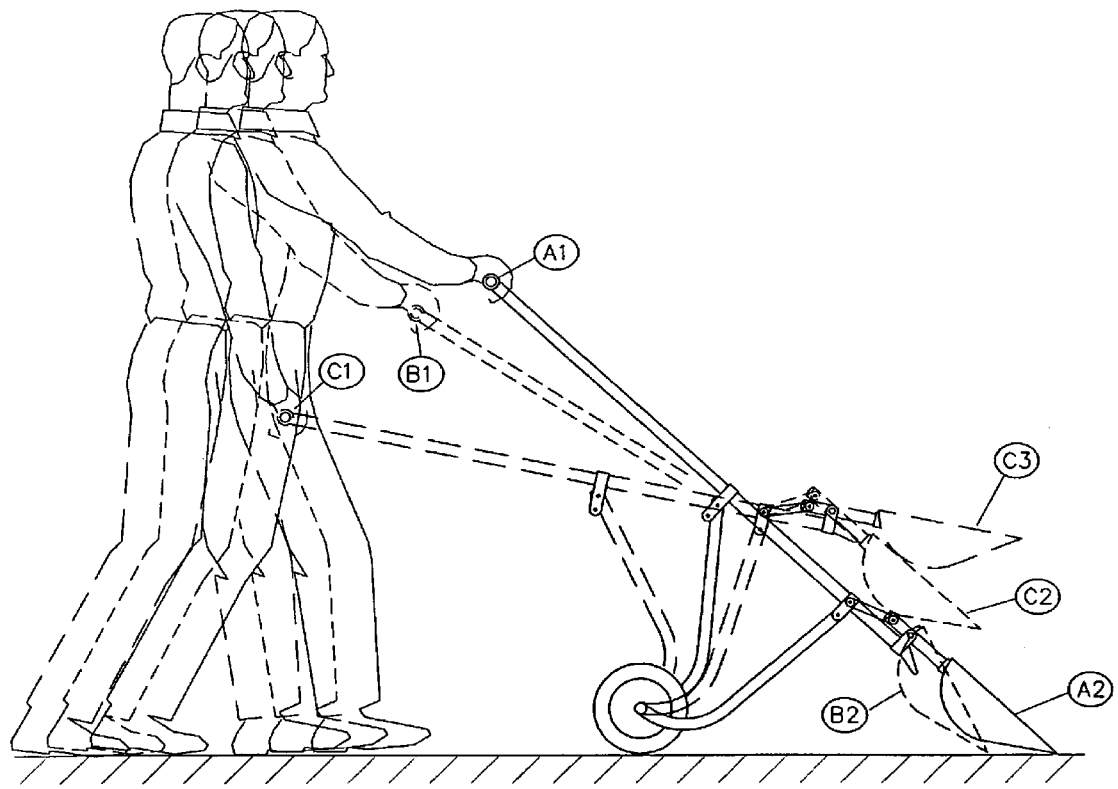
FIG. 9 is a combined sequences of operation diagram, indicating handle/shovel head relations to the operator at different sequences during operation.

As shown in FIG. 9
>A1=; Handle elevation at gathering mode
>A2=; Shovel head at gathering mode
>B1=; Handle elevation at initial launch
>B2=; Shovel head at initial launch.
>C1=; Handle elevations at final launch and launched-off
>C2=; Shovel head at final launch
>C3=; Shovel head at launched-off As shown in FIG. 10A. Shovel head in Loading utilizing springs arrangement; Shovel head 31 is resting on the ground at gathering mode with springs 35 in dormant state. Locking pin 54 is inserted through hole 25 in order to secure wheel assembly in ready-use operation.

Figure 10B:
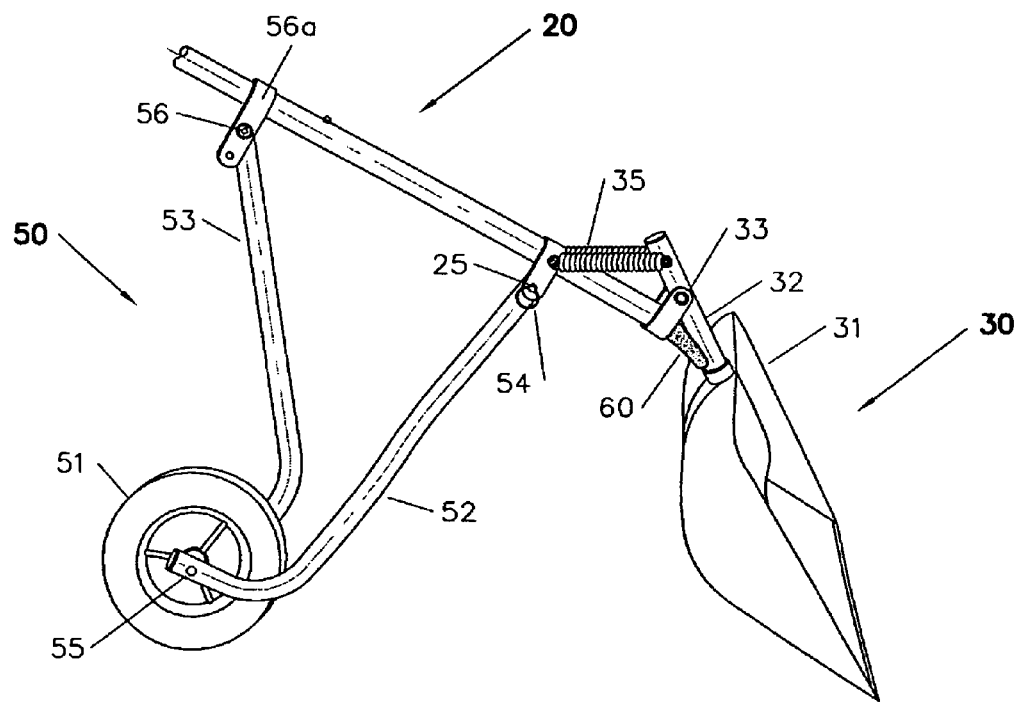
FIG. 10B is a close-up view of the tilting bucket assembly showing artificially loaded shovel head position utilizing the springs arrangement.
Figure 10A:
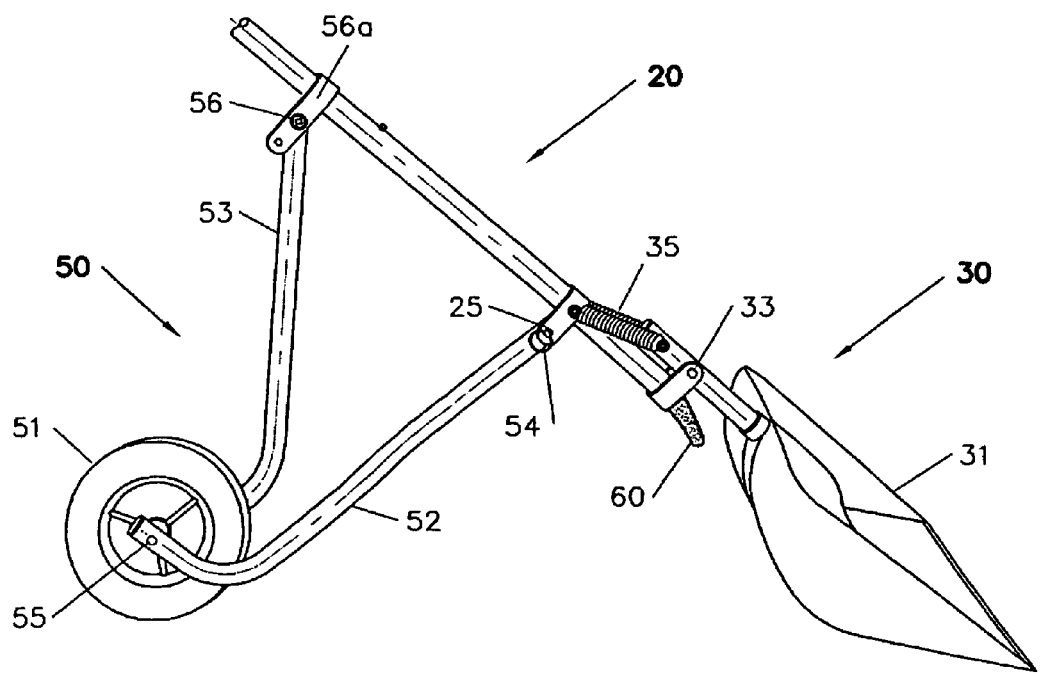
FIG. 10A is a close-up view of the tilting bucket assembly showing shovel head in loading position utilizing the springs arrangement.

Referring to FIG. 10B, this shows an artificially Loaded Shovel Head utilizing springs arrangement; Due to induced load cause by sudden jerk by operator on the other end, the springs 35 are extended and shovel head 31 tilts downward on its pivot 33. Shovel head shaft 32 then bottoms-out against plastic/rubber like coated bump stop 60. Wheel assembly 50 comprises of wheel 51, arm 52 on one side and arm 53 on the other side. Arm 52 is secured on one end with wheel axle 55 and the other end is secured with locking pin 54. Arm 53 is secured on one end with wheel axle 55 and the other end is secured with pin 56 (not shown). It is possible to use compression springs rather than extension springs as shown on FIG. 10B, by placing the compression springs on the same side as the shovel head in respect to pivot 33 (to the right of pivot 33) location in order to facilitate an equal effectiveness.

Figure 11B:
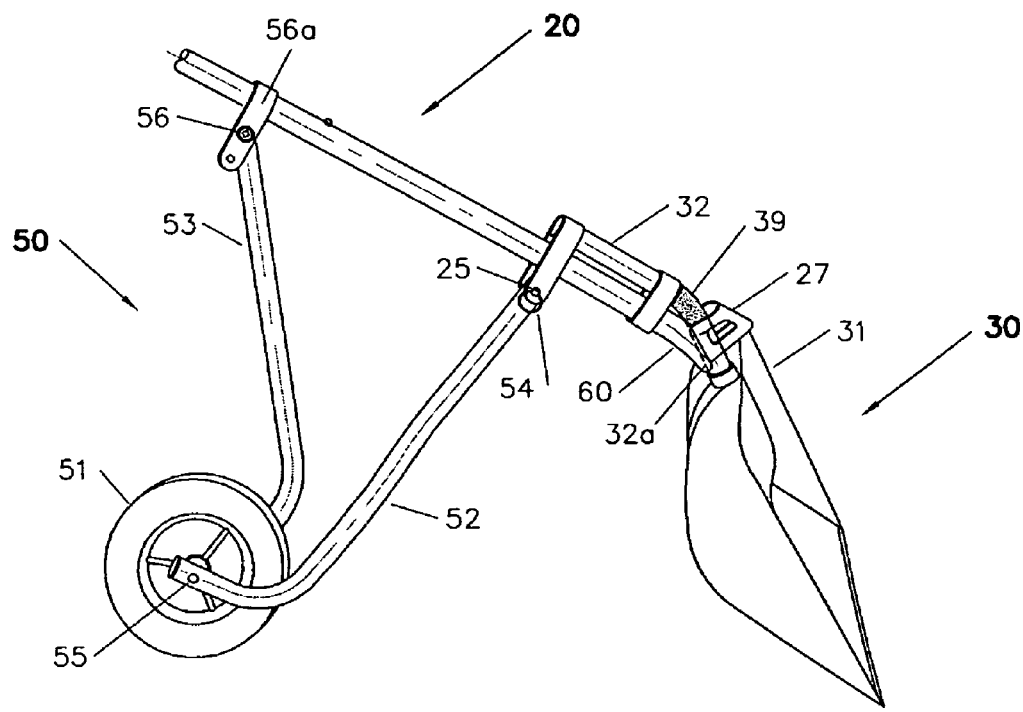
FIG. 11B is a close-up view of the tilting shovel assembly artificially loaded shovel head position utilizing alternate bendable plastic/rubber like compound material(s) arrangement.
Figure 11A:
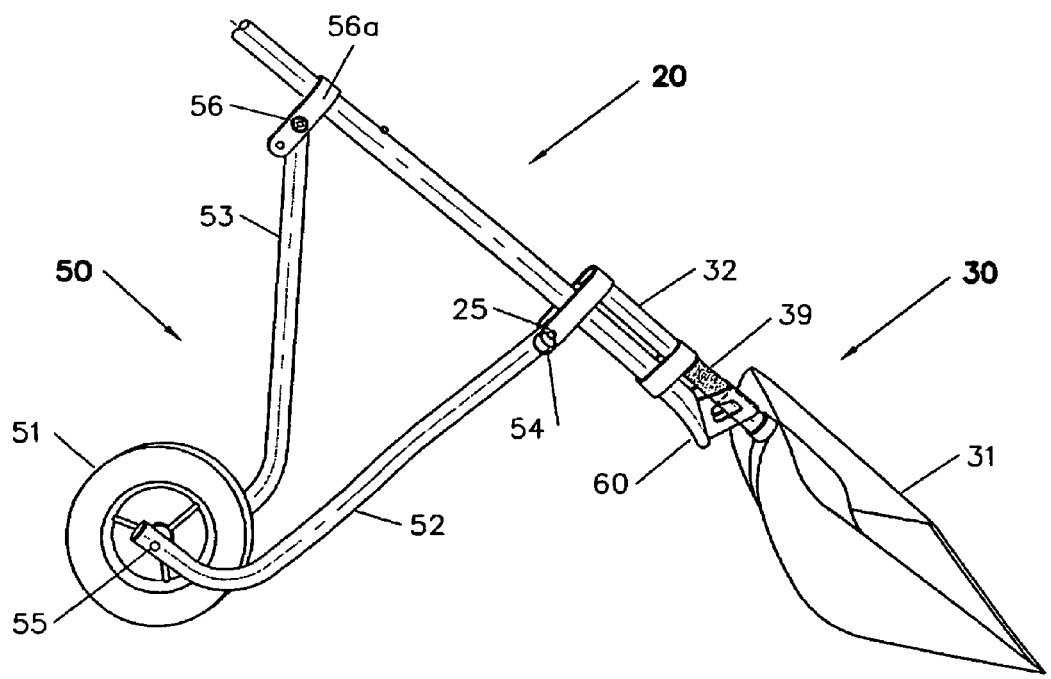
FIG. 11A is a close-up view of the tilting shovel assembly showing shovel head in loading position utilizing alternate bendable plastic/rubber like compound material(s) arrangement.

As shown in FIG. 11A. The Shovel utilizes an alternate bendable plastic/rubber like compound member 39. Shovel head 31 is resting on the ground at gathering mode with member 39 in dormant state.

As shown in FIG. 11B. The Shovel utilizes alternate bendable plastic/rubber like compound member 39. Due to induced load cause by sudden jerk by operator on the other end, the elastic 39 is bent and shovel head 31 tilted downward. Shovel head handle 32a then bottom-out against plastic/rubber like coated bump stop 24 60.

Figure 12:
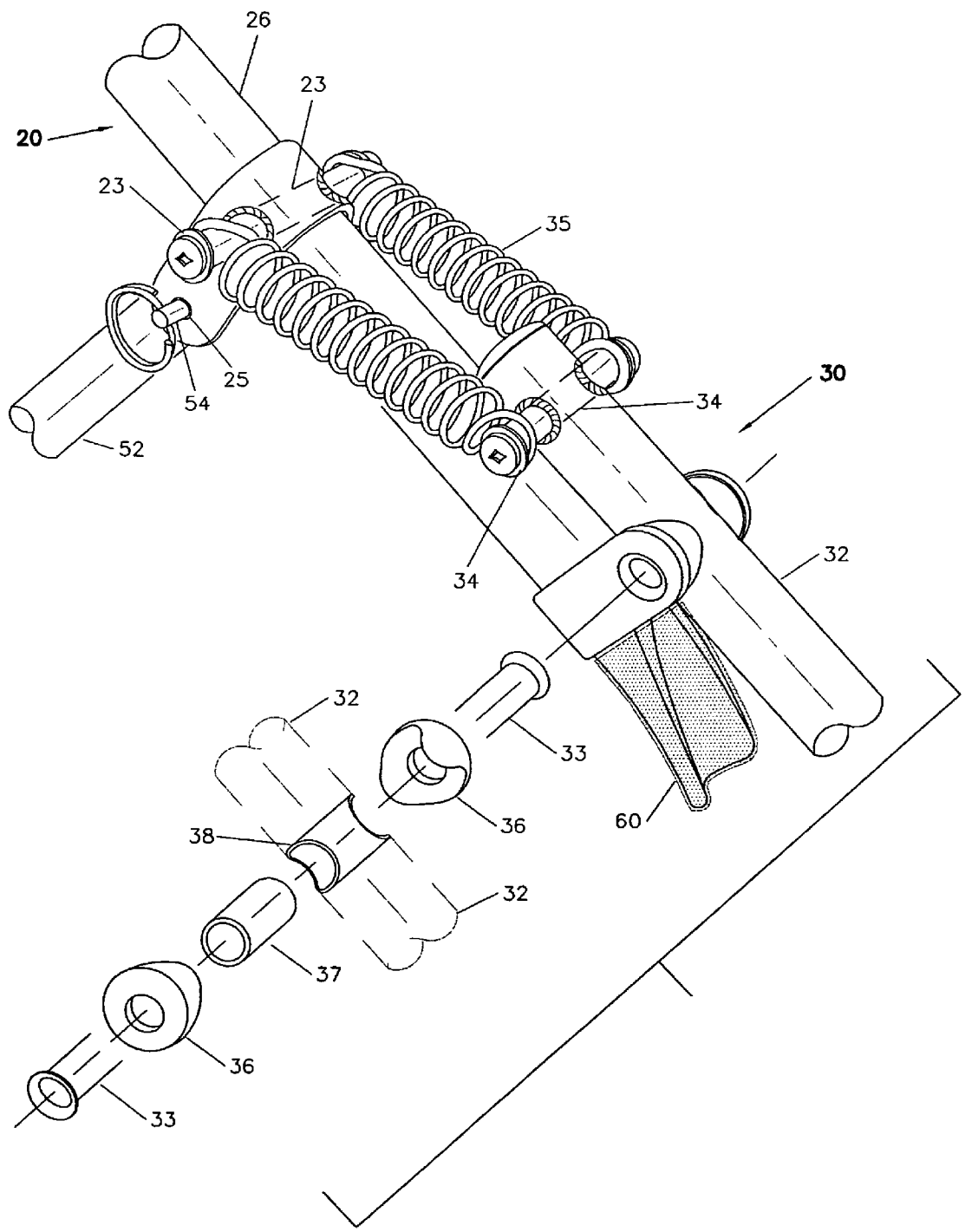
FIG. 12 is a close-up view of pivot assembly.

As shown in FIG. 12. Spring mounting pin 34 is inserted through shovel head shaft 32 and welded on both sides, shoulders to retain springs are provided on both ends of spring mounting pin 34. Spring mounting pin 23 is inserted through primary handle 26 and welded on both sides, shoulders to retain springs are provided on both ends of spring mounting pin 23. Metal sleeve 38 is inserted through shovel head shaft 32 and welded on both sides. Plastic like friction-free material bushing 37 then inserted in metal sleeve 38. Plastic like cove spacers 36 are provided on both sides of shovel head shaft 32. Finally, hollow metal axle 33 is inserted through pivot assembly with flares on both ends to retain the whole assembly together.

Figure 13B:
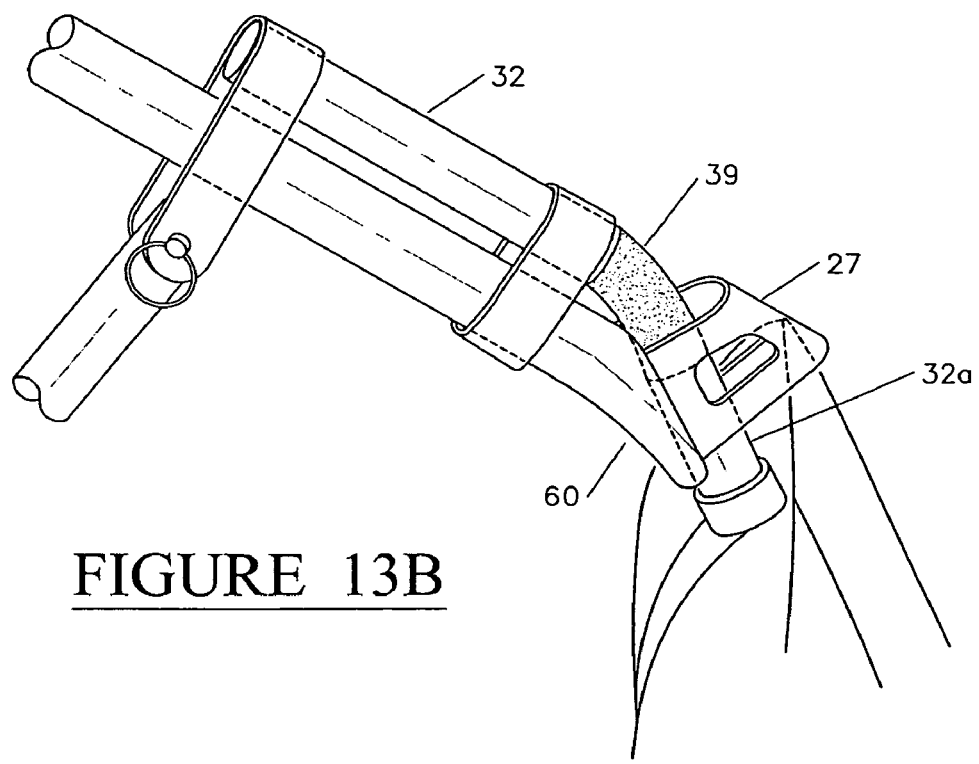
FIG. 13B is a close-up view of alternate bendable plastic/rubber like compound material assembly at bent stage; and, FIG. 14 is a close-up view of wheel assembly.
Figure 13A:
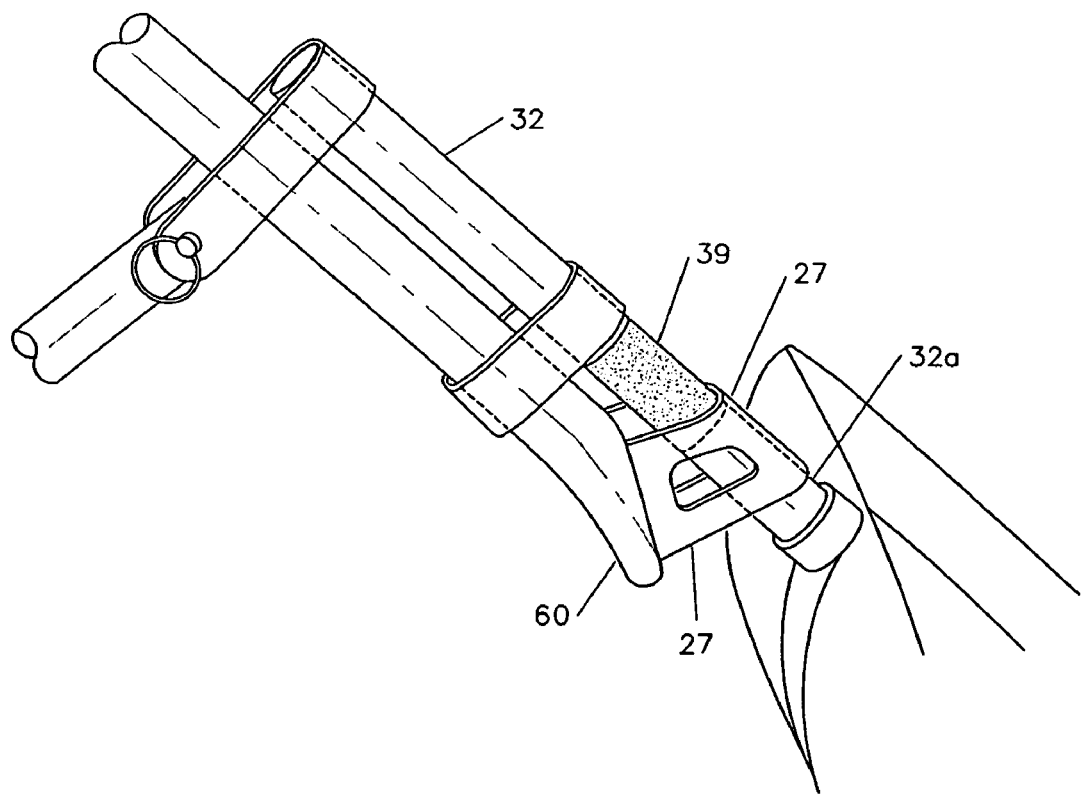
FIG. 13A is a close-up view of alternate bendable plastic/rubber like compound material assembly at dormant stage.

As shown in FIG. 13A the shovel head is mounted by means of alternate bendable plastic/rubber like compound member 39. One end is inserted in shovel head shaft 32 and the other end is inserted in shovel head stub 32a. Top half-round closure guide 27 is provided. The closure-sides to keep the stub 32a from moving side to side and allowing it to rotate freely in a vertical plane. The closure-top to provide stopper on the shovel head stub 32a from bending upward.

As shown in FIG. 13B. The Shovel utilizes alternate bendable plastic/rubber like compound member 39 bent due to artificial load on the shovel head.

Figure 14:
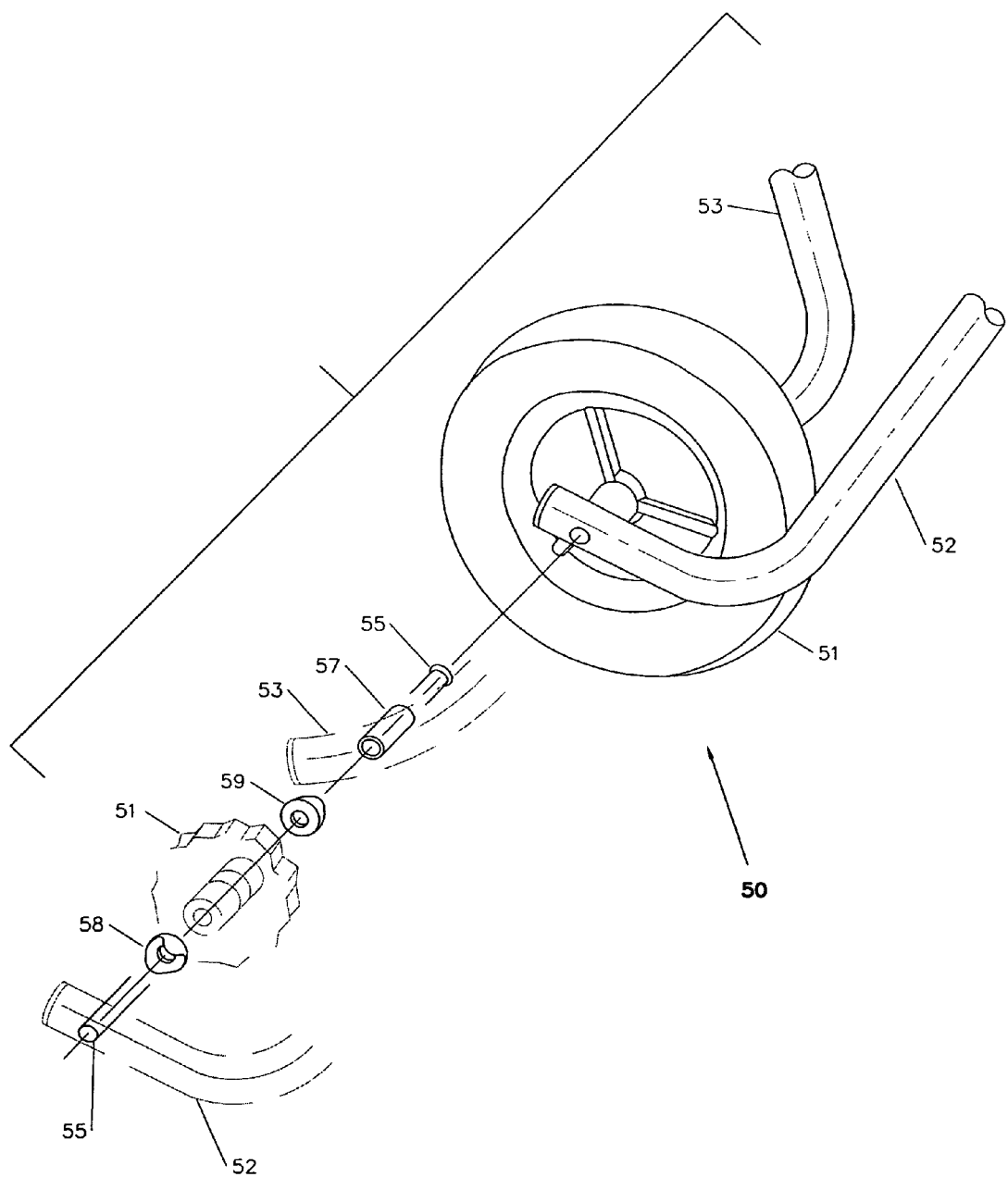

As shown in FIG. 14. Wheel axle 55 is inserted through arm 52 and welded on both sides. Plastic like cove spacers 58 and 59 are provided on both sides of the wheel 51. Metal sleeve 57 is inserted through arm 53 and welded on both sides. Wheel axle 55 is hollow, then inserted through wheel and again through metal sleeve 57 then flared on the end to retain the whole assembly together. It is possible for wheel assembly 50 to be folded as shown on previous FIG. 4 due to arm 53 rotate freely around the wheel axle 55 on one end and pin 56 on the other end.

The foregoing is a description of a preferred embodiment of the invention which is given here by way of example only. The invention is not to be taken as limited to any of the specific features as described, but comprehends all such variations thereof as come within the scope of the appended claims.

What is claimed is:

1. A device for removing and disposing of snow comprising:
   a main handle defining a hand grip end and a pivot end;
   a handle pivot on said pivot end of said main handle;
   a shovel shaft defining first and second shovel shaft ends;
   a pivot bearing on said shovel shaft located midway between said first end of said shovel shaft and said second end of said shovel shaft said pivot bearing being pivotally mounted on said handle pivot of said main handle, whereby said shovel shaft is swingable in a see-saw fashion on said handle pivot between first and second positions;
   a shovel head fixedly secured to said second end of said shovel shaft, and being moveable in unison therewith;
   a bump stop extending from said pivot end of said main handle, and lying alongside to but spaced from said shovel shaft and defining a limit for swinging of said shovel shaft, at said second position;
   spring means connected between said main handle and said first end of said shovel shaft operable to urge said shovel shaft into said first position, and said spring means being yieldable upon loading of said shovel head with snow to permit swinging of said shovel shaft into said second position, against said bump stop, and said spring means urging said shovel shaft and said shovel head to return back to said first position when the snow load is launched;
   a foldable wheel assembly connected to said main handle;

a first arm supporting said wheel assembly on one side of said wheel assembly; and a second arm supporting said wheel assembly on the opposite side thereof; said first arm being attached to said main handle at a first arm pivot and said second arm being attached to said main handle at a second arm pivot, wherein said first arm pivot is spaced apart from said second arm pivot.

2. The device of claim 1, including a detachable shaft, attachable to said main handle.

3. The device of claim 1, wherein the wheel assembly is foldable relative to said main handle for storage.

4. The device of claim 1, wherein the spring means is formed in part of bendable material.

5. The device of claim 1, wherein the launching of snow in the shovel head is responsive to an operator creating downward movement on said main handle, whereby the device then rotates toward the operator around the wheel assembly.

6. The device of claim 5, wherein after discharge of the snow off the shovel head, said spring means will return said shovel shaft and shovel head to their first position.

7. The device of claim 1, wherein said second arm is swingable relative to said wheel assembly, and is detachable from said second arm pivot for storage.

8. The device of claim 7 wherein said first arm pivot is attached to said main handle adjacent said hand grip end, and wherein said second arm pivot is attached to said main handle adjacent said pivot end of said main handle.

9. The device of claim 8 wherein said second arm pivot is slidable along said main handle, whereby said first and second arms can be folded alongside each other for storage.

* * * * *